United States Patent [19]

Feuer et al.

[11] 4,110,441

[45] Aug. 29, 1978

[54] GAMMA-L-GLUTAMYL CHOLAMINE PHOSPHATE

[75] Inventors: Laszlo Feuer; Arpad Furka; Ferenc Sebestyen; Jolan Hercsel nee Szepespataky; Erzsebet Bendefy nee Dobay, all of Budapest, Hungary

[73] Assignee: Chinoin Gyogyszer es Vegyeszeti Termekek Gyara Rt., Budapest, Hungary

[21] Appl. No.: 696,762

[22] Filed: Jun. 16, 1976

Related U.S. Application Data

[63] Continuation-in-part of Ser. No. 571,766, Apr. 25, 1975, abandoned.

[30] Foreign Application Priority Data

Apr. 29, 1974 [HU] Hungary .............................. FE 928
Mar. 26, 1975 [HU] Hungary .............................. CI 1558

[51] Int. Cl.$^2$ .......................... A01N 9/36; C07F 9/09
[52] U.S. Cl. ................................... 424/211; 260/944; 260/968
[58] Field of Search ......................... 260/944; 424/211

*Primary Examiner*—Anton H. Sutto
*Attorney, Agent, or Firm*—Karl F. Ross

[57] ABSTRACT

Gamma-L-glutamyl cholamine phosphate and beta-L-aspartyl cholamine phosphates are disclosed, the compounds having blood-sugar-level lowering and serum vitamin A increasing effect.

6 Claims, No Drawings

GAMMA-L-GLUTAMYL CHOLAMINE PHOSPHATE

CROSS REFERENCE TO RELATED APPLICATION

The present application is a continuation-in-part of Ser. No. 571,766, filed April 25, 1975, now abandoned.

FIELD OF THE INVENTION

This invention relates to novel amino acid derivatives namely gamma-L-glutamyl cholamine phosphate, and pharmaceutical compositions containing the same, as well as to a process for the preparation thereof.

DESCRIPTION OF THE INVENTION

Gamma-L-glutamyl-cholamine phosphate and beta-L-aspartyl cholamine phosphate, two of the compounds disclosed in said application, have been found to be effective therapeutically as the AGAS system, as well as on the tissues thereof, in certain ways as outlined below.

Each compound according to the invention exerts its activities in part directly, and in part through control of vitamin A metabolism, by the production of more polar vitamin A metabolites. This activity is similar to that exerted by parathormone on the 25-hydroxy-cholecalciferol-1-α-hydroxylase enzyme of the renal tubules. The above facts explain the wide and diverse biochemical, pharmacological and therapeutical activities of the compound according to the invention:
increase in serum vitamin A;
Transitory blood-sugar decrease.

The duration of the treatment with the compound according to the invention can vary widely. With an oral dose of 5 μg. of the chemically pure active substance administered three times a day some of the patients become symptom-free even after two weeks (e.g. in the case of rhino-laryngo-pharyngitis sicca). For the treatment of certain diseases one or two months are needed (e.g. parodontosis, Sjogren's syndrome), whereas in the case of other diseases treatment periods of three to six months are required (e.g. spondylosis ankylopoetica).

The compound according to the invention can be converted into cosmetical or pharmaceutical compositions for use in human or veterinary therapy. These compositions may contain the compounds according to the invention as the sole active ingredient or in combination with other biologically active substances. The active agents according to the invention are administered preferably three times a day in dosages of 50 to 500 nanograms/kg. body weight.

One tablet contains 2 to 20 micrograms, preferably about 10 micrograms of the active ingredient admixed with biologically inert carriers (e.g. lactose, starch) and customary auxiliary substances (e.g. granulating agents and lubricants), such as polyvinyl pyrrolidone, gelatine, talc, magnesium stearate and ultrafine silica.

Considering the very low concentration of the active substance, to obtain an even dispersion thereof in the tablet it is preferable to admix the active principle in the form of solution with the tablet mass prior to granulation and to prepare a homogeneous mixture using a kneeding machine. The small quantity of active material required allows its preparation on a large laboratory scale, even for the production of several billions of tablets, at an acceptable cost. The active principle is stable and therefore the tablets can be stored for long time. The active principle content of depot tablets or spansuled capsules may be between 10 to 30 μg.

Injectable preparations containing the active principle in powder ampoules, optionally in admixture with a biologically indifferent water-soluble diluent, contain preferably 5 to 10 μg. of active principle per ampoule. The parenteral application may be intramuscular, subcutaneous or intravenous. The active principle in the given concentrations does not irritate the tissues or vessel walls, and can be used in the form of an infusion as well.

Suppositories can be prepared with an active g., content of 2 to 20 μ., preferably 10 μg., using cocoa butter or any synthetic wax or fat (e.g. Imhausen mass, GFR) conventional for this purpose.

Ointments for dermatological or cosmetic purposes prepared with the usual hydrophilic or hydrophobic ointment bases (e.g. cholesterol, paraffin, glycerine, lanolin, linseed oil, etc.) can have an active principle content of 0.1 to 1.0 μg./g.

Aerolsol preparations can contain the active principle in a concentration of 0.1 to 1.0 μg./g. Perlingual tablets can have an active principle content of about 10 μg. per tablet and a degradation time of 0.5 to 1 hour.

The polymers with high molecular weights having sustained effect can also be prepared e.g. in the form of suspensions with an active principle content of 1 to 5 μg./g. Similarly, injectable preparations with sustained effect can be prepared from the polymers or from the salts of the compound according to the invention with organic bases of high molecular weights (e.g. protamine, histone). These compositions can contain the active principle in an amount of 10 to 20 μg. per ampoule.

The dermatological and cosmetic powders can have an active principle content of 0.1 to 1 μg./g., and contain the usual carriers (e.g. talc).

Eye drops used for opthalmologic purposes and the ointments miscible or immiscible with tears have an active principle content of 0.1 to 1.0 μg./g.

For pediatric purposes the most preferred dosage is 0.3 μg. of active principle per kg. of body weight.

All sterile compositions are prepared preferably by sterile filtration.

Several combinations of the above preparations containing the compound according to the invention increase, supplement or modify the desired preventive, therapeutic or cosmetic effect. Primarily, the following combinative supplementary components should be mentioned:

Vitamin A, vitamin C, vitamin E, vitamin K, trace elements, cortisone and its derivatives, progesterone, hormones of the thyroid gland, products of radiomimetic and immunosuppressive effects, psychopharmacons (especially tranquillizers or thymoleptics), organic silicon compounds, gerontological preparations, oral antidiabetics, antiphlogistics antihistamines, etc. The dosage of the components in the combination is generally identical with the usual therapeutic dosages when using them independently.

The compound according to the invention can be used as additives in therapeutic and nutrient premixes. Used in such compositions the compound increases the weight gain and decrease the vitamin A demand and/or increase the absorption and metabolism of vitamin A. The compounds improve the absorption and increase the blood level of trace elements. When used as feed additive, they can be administered to the animals in a daily oral dosage of 100 to 300, preferably about 200 nanograms/kg. body. This corresponds generally to a concentration of 1 to 2 μg. per kg. of feed (i.e. 1 to 2 mg./ton or 0.001 to 0.002 ppm) when admixed with the animal feed. Considering the very low concentration required, the compounds according to the invention can be admixed with vitamin premixes or microcapsules containing other valuable feed additives, or can be administered as an additive of the drinking water or the licking salt. The compounds according to the invention can also be used for veterinary purposes in forms similar to those applied in human therapy (e.g. for epithelization, wound healing and bone fractures).

The compound contains an α-substituted dicarboxylic acid moiety the ω-carboxy group of which is attached through an amido bond to a primary or secondary amino group containing in the alkyl side chain, beside other substituents, a strongly acidic group in the ω-position.

The compound can be prepared according to the invention as follows: reacting carbobenzyloxy-L-glutaminic-acid-(alpha-benzyl)-gamma-p-nitrophenol ester in a mixture of pyridine and water with cholamine phosphate and trieghylamine to produce carbo-benzyloxy-gamma-(alphabenzyl)-L-glutamyl-cholamine phosphate; and catalytically hydrogenating said carbobenzyloxy-gamma-(alpha-benzyl)-L-glutamyl-cholamine phosphate to produce gamma-L-glutamyl-cholamine phosphate.

EXAMPLE 1

1.083 g. (2.2 mmoles) of carbobenzyloxy-L-glutaminic acid-(α-benzyl)-gamma-p-nitrophenyl ester are dissolved in 6 ml. of a 2:1 mixture of pyridine and water, and 282 mg. (2 mmoles) of cholamine phosphate (US Pat. No. 2,730,542) and 0.87 ml. (6.2 mmoles) of triethylamine are added to the solution. The mixture is allowed to stand at room temperature for 72 hours and then it is evaporated in vacuo. The residue is processed as described in Example 23 of said patent. 1.25 g. of carbobenzyloxy-gamma-(α-benzyl)-L-glutamyl-cholamine phosphate are obtained.

EXAMPLE 2

1.25 g. of the product obtained according to Example 1 are subjected to catalytic hydrogenation in order to remove the protecting group. The hydrogenation and the processing of the reaction mixture are identical with those described in Example 24. 470 mg. (91%) of gamma-L-glutamyl-cholamine phosphate are obtained. On the basis of paper elecgtrophoresis this substance contains about 15 to 20% of cholamine phosphate as impurity. The crude product can be purified e.g. by electrophoresis.

In paper electrophoresis performed at pH 6.5 and 1.8, respectively, the substance always migrates towards the cathode. Relative motility values (related to cysteinic acid): 0.75 and 0.36, respectively. $R_f = 0.18$ (in a 15:10:3:12 mixture of n-butanol, pyridine, glacial acetic acid and water).

EXAMPLE 3

526 mg. (1.1 mmoles) of carbobenzyloxy-L-aspartic acid-(α-benzyl)-β-nitrophenyl ester (Chem. Ber 97, 1789 1964) are dissolved in 5 ml. of pyridine. The solution is cooled to 0° C., and a solution of 125 mg. (1 mmole) of taurine in 2 ml. of water is added in small portions followed with 0.28 ml. (2 mmoles) of triethylamine. The reaction mixture is allowed to stand at room temperature for 48 hours, and then evaporated in vacuo. The residue is dissolved in 5 ml. of water, and 1 N hydrochloric acid is added dropwise to the solution until the disappearance of the yellow color. The solution is washed with 10×5 ml. of ether in order to remove p-nitrophenol. The aqueous phase is evaporated in vacuo. 478 mg. of carbobenzyloxy-β-(α-benzyl)-L-aspartyl-taurine are obtained.

EXAMPLE 4

The total amount of the product obtained according to Example 3 is dissolved in 6 ml. of 50% aqueous ethanol, 100 mg. of 10% palladium-on-carbon catalyst are added, and hydrogen is bubbled through the suspension for 4 hours. The catalyst is filtered off, the filtrate is evaporated in vacuo, and the triethylamine is removed from the residue as described in Example 24. 172 mg. (71%) of β-L-aspartyl-taurine are obtained. The product contains a small amount of taurine as impurity, which can be removed e.g. by electrophoresis.

In paper electrophoresis performed at pH 6.5 and 1.8, respectively, the substance always migrates towards the cathode. Relative motility values (related to cysteinic acid): 0.77 and 0.58, respectively. $R_f = 0.16$ (in a 15:10:3:12 mixture of n-butanol, pyridine, glacial acetic acid and water.

EXAMPLE 5

526 mg. (1.1 mmoles) of carbobenzyloxy-L-aspartic acid-(α-benzyl)-β-p-nitrophenyl ester are reacted with 139 mg. (1 mmole) of homotaurine as described in Example 3 to yield carbobenzyloxy-β-(α-benzyl)-L-aspartyl-homotaurine.

EXAMPLE 6

The product of Example 5 is subjected to catalytic hydrogenation as described in Example 24 of said application. 203 mg. of β-L-aspartyl-homotaurine are obtained; yield: 84%.

In paper electrophoresis performed at pH 6.5 and 1.8, respectively, the substance always migrates towards the cathode. Relative motility values (related to cysteinic acid): 0.72 and 0.53, respectively, $R_f = 0.17$ (in a 15:10:3:12 mixture of n-butanol, pyridine, glacial acetic acid and water).

EXAMPLE 7

Carbobenzyloxy-L-aspartic acid-(α-benzyl)-β-p-nitrophenyl ester is reacted with cholamine phosphate as described in Example 1 to obtain carbobenzyloxy-β-(α-benzyl)-L-aspartyl-cholamine phosphate.

EXAMPLE 8

The substance obtained in Example 7 is subjected to catalytic hydrogenation as described in Example 24 of said application to obtain β-L-aspartyl-cholamine phosphate.

In paper electrophoresis performed at pH 6.5 and 1.8, respectively, the substance always migrates towards the cathode. Relative motility values (related to cysteinic acid): 0.81 and 0.40, respectively. $R_f = 0.14$ (in a 15:10:3:12 mixture of n-butanol, pyridine, glacial acetic acid and water).

EXAMPLE 9

Carbobenzyloxy-gamma-(α-benzyl)-L-glutamyl-cholamine is prepared by the method generally applicable for the preparation of glutaminic acid-gamma-amides (Acta Chim. Acad. Sci. Hung. 64, 285 1970). 4.14 g. of the obtained substance are dissolved in 50 ml. of absolute pyridine, and 9 g. of diphenylphosphoryl chloride are added. The mixture is maintained at 0° C. for 12 hours, then diluted with 80 ml. of chloroform. The separated substance is filtered off, washed with dilute hydrochloric acid and then with water, finally dried in a desiccator over solid potassium hydroxide. The obtained substance is dissolved in 15 ml. of 3.3 molar hydrogen bromide in glacial acetic acid. The solution is allowed to stand for 15 minutes and then it is evaporated in vacuo at 35° C. The residue is dried over solid potassium hydroxide. The dry substance is dissolved in 30 ml. of 1 N sodium hydroxide solution. The mixture is allowed to stand at room temperature for one hour, thereafter acidified to pH 4 with acetic acid, and extracted with 3×30 ml. of ether in order to remove the by-products (phenol and benzyl alcohol). The aqueous phase is passed through a column filled with Dowex 50 ion exchanger (H+ cycle), and the column is eluted with water. The eluate is evaporated in vacuo, and the residue is recrystallized from a 2:1 mixture of acetone and water. 0.8 g. of gamma-L-glutamyl-cholamine phosphate are obtained.

EXAMPLE 10

4.68 ml. (50 mmoles) of phosphorous oxychloride are added dropwise to 1.8 ml. of water under cooling and stirring (Biochem. Preparations 6, 76 1958), and 1.9 g. (10 mmoles) of gamma-L-glutamyl-cholamine (prepared from carbobenzyloxy-(α-benzyl)-L-glutamyl-cholamine, see Example 38) are added in small portions to the stirred mixture. The mixture is stirred at 60° C. for 2 hours, then it is allowed to cool, and 0.72 ml. of water are added dropwise to the stirred mixture. The mixture is allowed to stand at room temperature for 2 hours, and then 10 ml. of 96% ethanol and 10 ml. of ether are added dropwise. The reaction mixture is allowed to stand at 4° C. overnight, then 5 ml. of 96% ethanol are added. The separated substance is filtered off, washed with ethanol and ether, and recrystallized from aqueous ethanol. 1.75 g. of gamma-L-glutamyl-cholamine phosphate are obtained.

We claim:

1. A method of reducing the blood-sugar level and increasing the serum vitamin A level which comprises administering an effective amount of gamma-L-glutamyl cholamine phosphate.

2. A pharamaceutical composition effective in reducing the blood-sugar level and increasing the serum vitamin A level in mammals which consists essentially of gamma-L-glutamyl cholamine phosphate in a pharmaceutically acceptable carrier.

3. A compound selected from the group which consists of gamma-L-glutamyl cholamine phosphate, beta-aspartyl cholamine phosphate and pharmaceutically effective salts thereof.

4. gamma-L-glutamyl cholamine phosphate.

5. A process for producing gamma-L-glutamyl-cholamine phosphate which comprises the steps of reacting carbobenzyloxy-L-glutaminic-acid-(alpha-benzyl)-gamma-p-nitrophenol ester in a mixture of pyridine and water with cholamine phosphate and triethylamine to produce carbo-benzyloxy-gamma-(alphabenzyl)-L-glutamyl-cholamine phosphate; and catalytically hydrogenating said carbo-benzyloxy-gamma-(alpha-benzyl)-L-glutamyl-cholamine phosphate to produce gamma-L-glutamyl-cholamine phosphate.

6. A method of making gamma-L-glutamyl cholamine phosphate which comprises the step of splitting off the carbobenzyloxi group and removing the alpha-benzyl group of carbobenyloxigamma-(alpha-benzyl)-L-glutamyl cholamine phosphate in pyridine and diphenyl phosphoryl chloride and dissolving the resulting substance in hydrogen bromide and glacial acetic acid.

* * * * *